United States Patent
Morrow

(10) Patent No.: US 12,390,436 B1
(45) Date of Patent: Aug. 19, 2025

(54) MUTATIONS IN MITOCHONDRIAL ENZYME GPT2 CAUSE METABOLIC DYSFUNCTION AND NEUROLOGICAL DISEASE WITH DEVELOPMENTAL AND PROGRESSIVE FEATURES

(71) Applicant: Brown University, Providence, RI (US)

(72) Inventor: Eric M. Morrow, Barrington, RI (US)

(73) Assignee: BROWN UNIVERSITY, Providence, RI (US)

( * ) Notice: Subject to any disclaimer, the term of this patent is extended or adjusted under 35 U.S.C. 154(b) by 470 days.

(21) Appl. No.: 17/322,497

(22) Filed: May 17, 2021

Related U.S. Application Data

(60) Provisional application No. 63/025,740, filed on May 15, 2020.

(51) Int. Cl.
| | |
|---|---|
| *A61K 31/225* | (2006.01) |
| *A61K 31/198* | (2006.01) |
| *A61K 49/00* | (2006.01) |
| *A61K 49/08* | (2006.01) |
| *A61P 3/00* | (2006.01) |
| *A61P 25/00* | (2006.01) |
| *C12Q 1/6883* | (2018.01) |

(52) U.S. Cl.
CPC .......... *A61K 31/225* (2013.01); *A61K 31/198* (2013.01); *A61K 49/0008* (2013.01); *A61P 3/00* (2018.01); *A61P 25/00* (2018.01); *C12Q 1/6883* (2013.01); *C12Q 2600/156* (2013.01)

(58) Field of Classification Search
CPC .... A61K 31/225; A61K 31/198; A61K 49/08; A61P 3/00; A61P 25/00; C12Q 1/6883; C12Q 2600/156
See application file for complete search history.

(56) References Cited

U.S. PATENT DOCUMENTS

2016/0265057 A1    9/2016    Smith et al.

OTHER PUBLICATIONS

Alanine, 2025, https://draxe.com/nutrition/alanine-benefits/.*
Triheptanoin, 2025,https://en.wikipedia.org/wiki/Triheptanoin.*
"Consideration of Sex as A Biological Variable in NIH-Funded Research", In NOT-OD-15-102 (Bethesda, MD: National Institutes of Health, U.S. Department of Health and Human Services), available at <https://orwh.od.nih.gov/sites/orwh/files/docs/NOT-OD-15-102_Guidance.pdf>, accessed on Jun. 4, 2020, 3 pages.
"Economic Costs Associated with Mental Retardation, Cerebral Palsy, Hearing Loss, and Vision Impairment—United States, 2003", Centers for Disease Control and Prevention (CDC), MMWR Morb Mortal Wkly Rep., vol. 53, No. 3, Jan. 30, 2004, pp. 57-59.
Aman, et al., "The Aberrant Behavior Checklist: A Behavior Rating Scale for the Assessment of Treatment Effects", American Journal of Mental Deficiency, vol. 89, No. 5, 1985, pp. 485-491.
Arlotta, et al., "Neuronal Subtype-Specific Genes That Control Corticospinal Motor Neuron Development in Vivo", Neuron vol. 45, 2005, pp. 207-221.
Battaglia, et al., "Placental Transport and Metabolism of Amino Acids", Placenta, vol. 22, 2001, pp. 145-161.
Blackstone, Craig, "Cellular Pathways of Hereditary Spastic Paraplegia", Annual Review of Neuroscience, vol. 35, 2012, pp. 25-47.
Boyko, et al., "Brain to Blood Glutamate Scavenging as A Novel Therapeutic Modality: A Review", J Neural Transm., vol. 121, No. 8, Aug. 2014, pp. 971-979.
Camp, et al., "Phenylketonuria Scientific Review Conference: State of the Science and Future Research needs", Molecular Genetics and Metabolism, vol. 112, No. 2, 2014, 36 pages.
Celis, et al., "Loss of Function Mutation in Glutamic Pyruvate Transaminase 2 (GPT2) causes Developmental Encephalopathy", Journal of Inherited Metabolic Disease, vol. 38, 2015, 8 pages.
Chow, et al., "Adaptive Design Methods in Clinical Trials—A Review", Orphanet Journal of Rare Diseases, vol. 3, 2008, 13 pages.
Connell, et al., "Quantitative Gait Analysis Using a Motorized Treadmill System Sensitively Detects Motor Abnormalities in Mice Expressing ATPase Defective Spastin", Plos One, vol. 11, 2016, pp. 1-16.
Fink, et al., "Comprehensive Corticospinal Labeling with Mu-Crystallin Transgene Reveals Axon Regeneration after Spinal Cord Trauma in ngr1-/- Mice", The Journal of Neuroscience, vol. 35, No. 46, Nov. 18, 2015, pp. 15403-15418.
Fink, John K, "Hereditary Spastic Paraplegia: Clinical Principles and Genetic Advances", Seminars in Neurology, vol. 34, No. 3, 2014, pp. 293-305.
Fink, et al., "Reorganization of Intact Descending Motor Circuits to Replace Lost Connections After Injury", Neurotherapeutics, vol. 13, 2016, pp. 370-381.
Francis, et al., "Dietary Triheptanoin Rescues Oligodendrocyte Loss, Dysmyelination and Motor Function in The Nur7 Mouse Model of Canavan Disease", Journal of Inherited Metabolic Disease, vol. 37, 2014, pp. 369-381.
Genc, et al., "Complexity of Generating Mouse Models to Study the Upper Motor Neurons: Let US Shift Focus from Mice to Neurons", International Journal of Molecular Sciences, vol. 20, 2019, pp. 1-26 pages.
Hadera, et al., "Triheptanoin Partially Restores Levels of Tricarboxylic Acid Cycle Intermediates in the Mouse Pilocarpine Model of Epilepsy", Journal of Neurochemistry, vol. 129, 2014, pp. 107-119.
Hao, et al., "Oncogenic PIK3CA Mutations Reprogram Glutamine Metabolism in Colorectal Cancer", Nature Communications, vol. 7, 2016, pp. 1-13.
Hengel, et al., "GPT2 Mutations Cause Developmental Encephalopathy with Microcephaly and Features of Complicated Hereditary Spastic Paraplegia", Clinical Genetics, vol. 94, 2018, 10 pages.

(Continued)

*Primary Examiner* — Sun Jae Yoo
(74) *Attorney, Agent, or Firm* — Adler Pollock & Sheehan P.C.

(57) ABSTRACT

The invention provides compounds and methods for treating a genetic disorder in childhood resulting from a mutation in the gene for the enzyme glutamate pyruvate transaminase 2 (gpt2). The mutation is a signature of metabolic defects.

4 Claims, 3 Drawing Sheets

(56) References Cited

OTHER PUBLICATIONS

Higashimori, et al., "Peripheral Axon Caliber and Conduction Velocity are Decreased After Burn Injury in Mice", Muscle & Nerve, vol. 31, May 2005, pp. 610-620.

Hochberg, et al., "More Powerful Procedures for Multiple Significance Testing", Statistics in Medicine, vol. 9, 1990, pp. 811-818.

Kaymakcalan, et al., "Novel Compound Heterozygous Mutations in GPT2 Linked to Microcephaly, and Intellectual Developmental Disability with or without Spastic Paraplegia", American Journal of Medical Genetics Part A, vol. 176, 2017, pp. 1-5.

Kim, et al., "Mitochondrial GPT2 Plays a Pivotal Role in Metabolic Adaptation to the Perturbation of Mitochondrial Glutamine Metabolism", Oncogene, vol. 38, 2019, 10 pages.

Landrum, et al., "ClinVar: Public Archive of Interpretations of Clinically Relevant Variants", Nucleic Acids Research, vol. 44, 2016, pp. D862-D868.

Landrum, et al., "ClinVar: Public Archive of Relationships Among Sequence Variation and Human Phenotype", Nucleic Acids Research, vol. 42, 2013, pp. D980-D985.

Liang, et al., "The Red Nucleus and The Rubrospinal Projection in The Mouse", Brain Struct Funct., vol. 217,, 2012, pp. 221-232.

Lobo-Prada, et al., "A Homozygous Mutation in GPT2 Associated with Nonsyndromic Intellectual Disability in a Consanguineous Family from Costa Rica", IMD Reports, vol. 36, 2017, 8 pages.

Maxwell, et al., "α-Motor Neurons are Spared from Aging while their Synaptic Inputs Degenerate in Monkeys and Mice", Aging Cell, vol. 17, 2018, pp. 1-12.

O'Kane, et al., "Na+-Dependent Neutral Amino Acid Transporters A, ASC, and N of the Blood-Brain Barrier: Mechanisms for Neutral Amino Acid Removal", AJP Endocrinology and Metabolism, vol. 287, 2004, pp. E622-E629.

Oldendorf, William H, "Brain Uptake of Radiolabeled Amino Acids, Amines, and Hexoses after Arterial Injection", American Journal of Physiology, vol. 221, No. 6, Dec. 1971, pp. 1629-1639.

Ouyang, et al., "GPT2 Mutations in Autosomal Recessive Developmental Disability: Extending the Clinical Phenotype and Population Prevalence Estimates", Human Genetics, vol. 138, 2019, 18 pages.

Ouyang, et al., "Mutations in Mitochondrial Enzyme GPT2 Cause Metabolic Dysfunction and Neurological Disease with Developmental and Progressive Features", PNAS, vol. 113, No. 38, Sep. 6, 2016, pp. E5598-E5607.

Owen, et al., "The Key Role of Anaplerosis and Cataplerosis for Citric Acid Cycle Function", Journal of Biological Chemistry, vol. 277, No. 34, 2002, pp. 30409-30412.

Ozdinler, et al., "Corticospinal Motor Neurons and Related Subcerebral Projection Neurons Undergo Early and Specific Neurodegeneration in hSOD1G93A Transgenic ALS Mice", The Journal of Neuroscience, vol. 31, No. 11, Mar. 16, 2011, pp. 4166-4177.

Park, et al., "Anaplerotic Triheptanoin Diet Enhances Mitochondrial Substrate Use to Remodel the Metabolome and Improve Lifespan, Motor Function, and Sociability in MeCP2-Null Mice", Plos One, vol. 9, No. 10, Oct. 2014, pp. 1-22.

Schmued, et al., "Fluoro-Jade B: A High Affinity Fluorescent Marker for The Localization of Neuronal Degeneration", Brain Research, vol. 874, No. 2, 2000, pp. 123-130.

Smith, et al., "Addiction to Coupling of the Warburg Effect with Glutamine Catabolismin Cancer Cells", Cell Reports, vol. 17, Oct. 11, 2016, pp. 821-836.

Sugita, et al., "VAChT Overexpression Increases Acetylcholine at the Synaptic Cleft and Accelerates Aging of Neuromuscular Junctions", Skeletal Muscle, vol. 6, No. 31, 2016, pp. 1-17.

Valdez, et al., "Attenuation of Age-Related Changes in Mouse Neuromuscular Synapses by Caloric Restriction and Exercise", Proceedings of the National Academy of Sciences, vol. 107, No. 33, Aug. 17, 2010, pp. 14863-14868.

Vockley, et al., "UX007 for the Treatment of Long Chain-Fatty Acid Oxidation Sisorders: Safety and Efficacy in Children and Adults following 24 weeks of Treatment", Molecular Genetics and Metabolism, vol. 120, 2017, pp. 1-8.

Willis, et al., "Anticonvulsant Effects of a Triheptanoin Diet in Two Mouse Chronic Seizure Models", Neurobiology of Disease, vol. 40, 2010, pp. 565-572.

Yamaguchi, et al., "Histological Analysis of Neurodegeneration in the Mouse Brain", Chapter 8, Necrosis: Methods and Protocols, Methods in Molecular Biology, vol. 1004, 2013, pp. 91-113.

Zhu, et al., "Ablation of NF1 Function in Neurons Induces Abnormal Development of Cerebral Cortex and Reactive Gliosis in the Brain", Genes and Development, vol. 15, 2001, pp. 859-876.

* cited by examiner

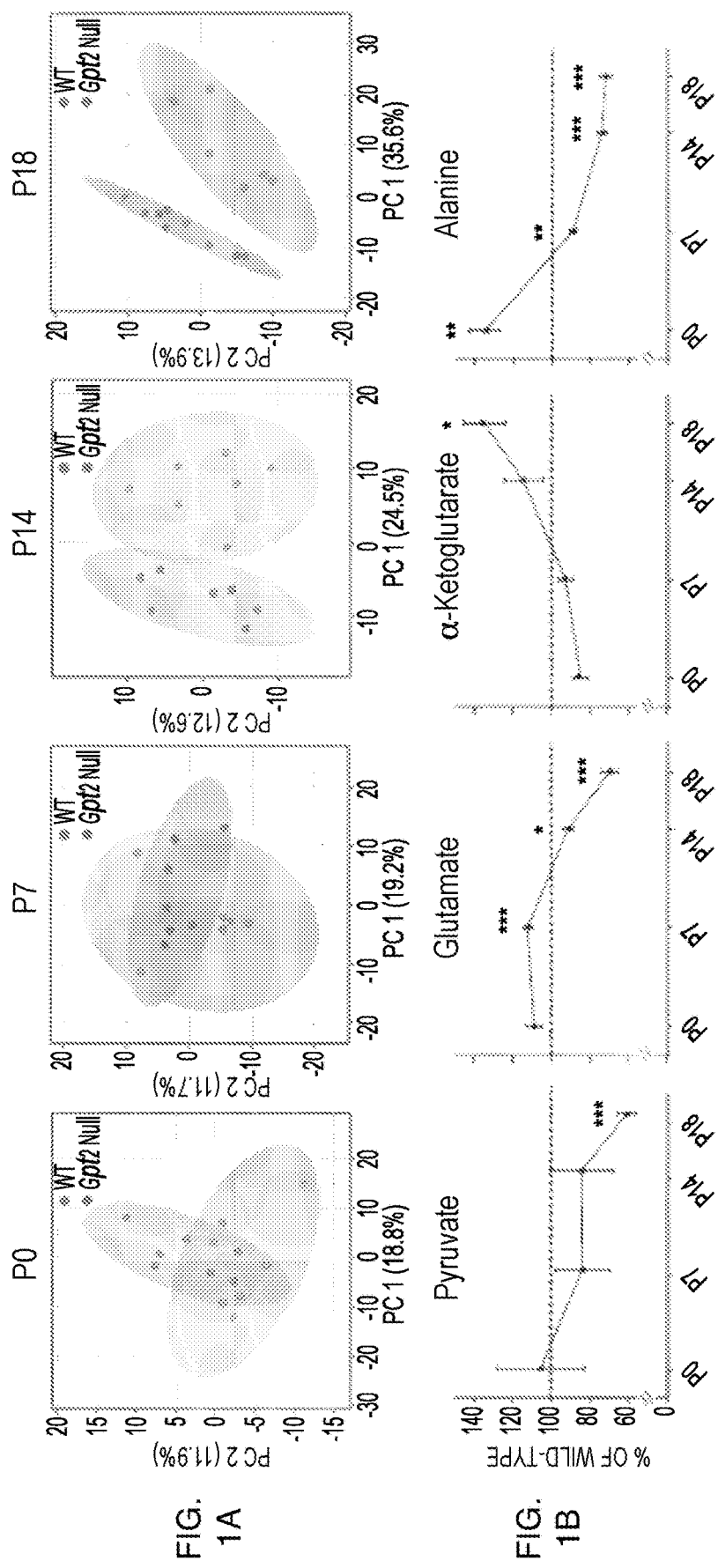

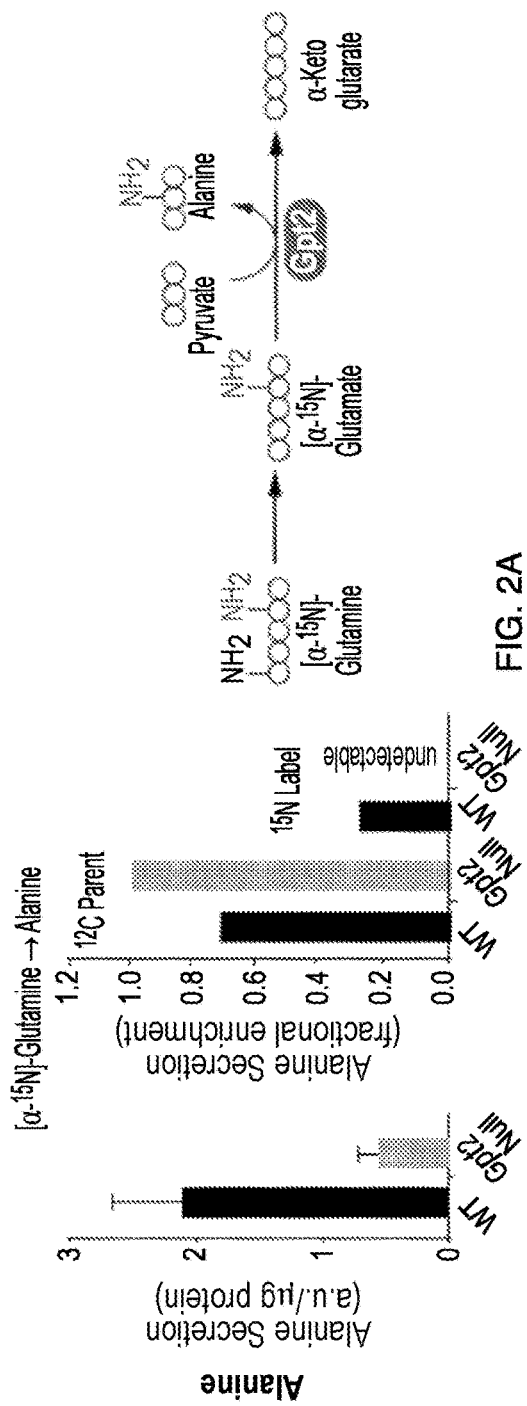
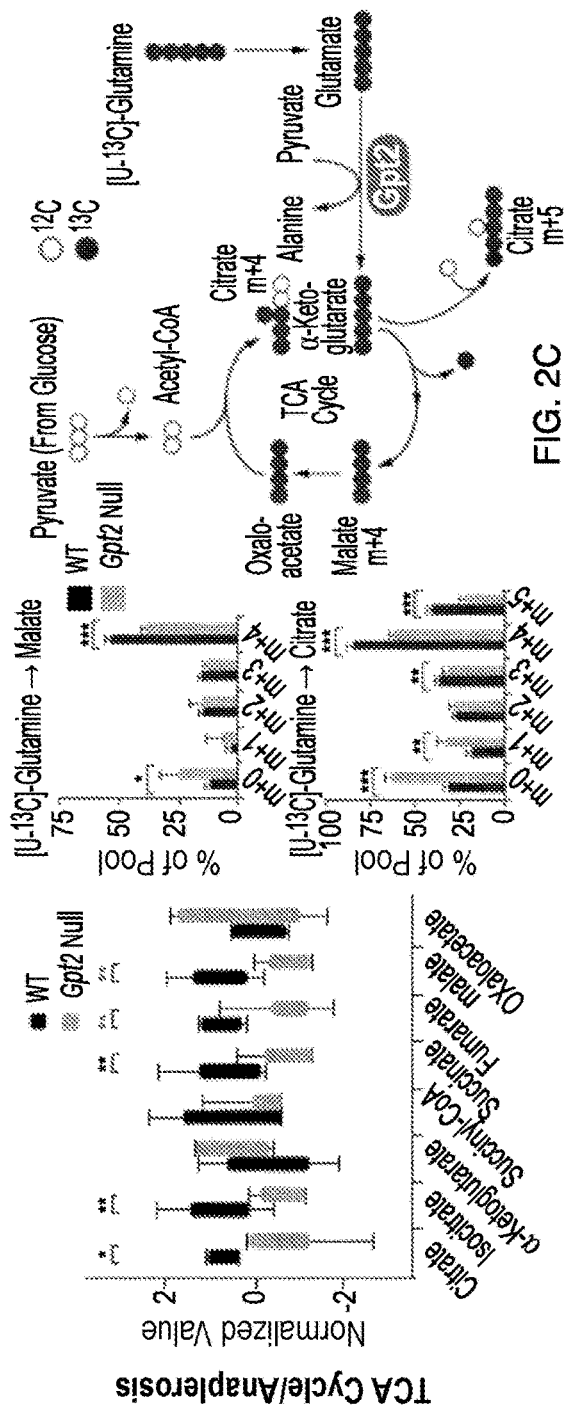

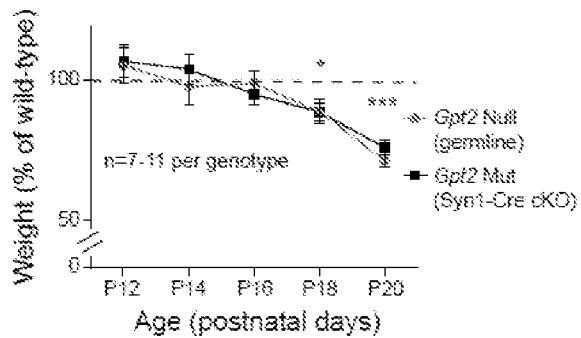
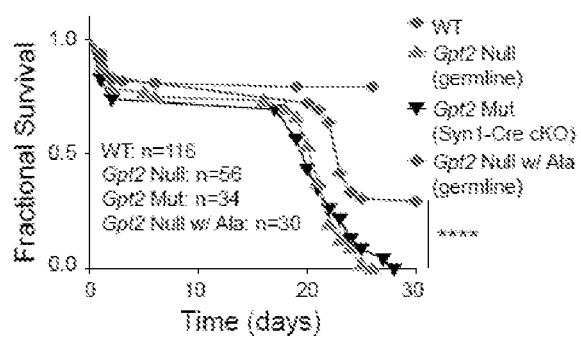
FIG. 3A
FIG. 3B
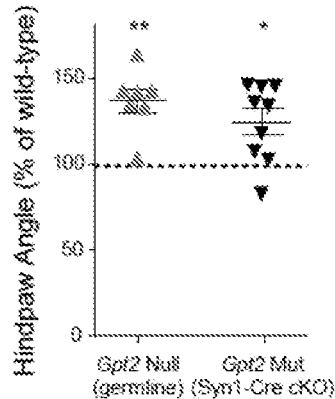
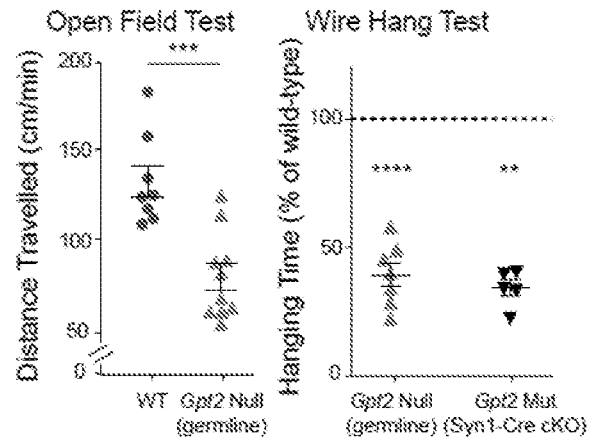
FIG. 3C
FIG. 3D
FIG. 3E
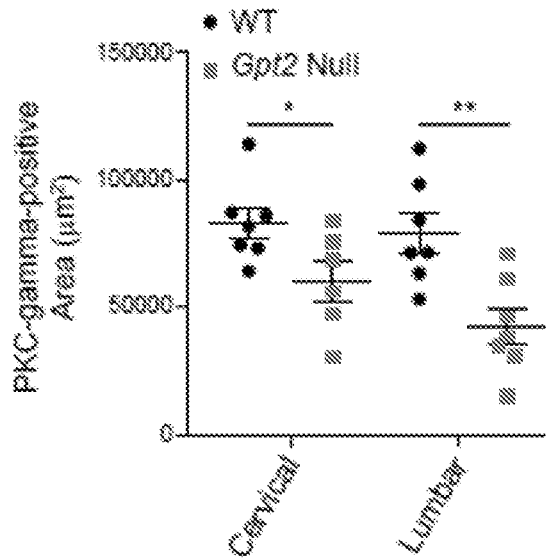
FIG. 4

MUTATIONS IN MITOCHONDRIAL ENZYME GPT2 CAUSE METABOLIC DYSFUNCTION AND NEUROLOGICAL DISEASE WITH DEVELOPMENTAL AND PROGRESSIVE FEATURES

FIELD OF THE INVENTION

This invention generally relates to nucleic acid products used in the analysis of nucleic acids, e.g., primers or probes for diseases caused by alterations of genetic material and treatments for the identified genetic diseases.

REFERENCE TO RELATED APPLICATIONS

This patent matter claims priority under 35 U.S.C. § 119 (e) to provisional patent application U.S. Ser. No. 63/025, 740, filed May 15, 2020, titled "Mutations in mitochondrial enzyme GPT2 cause metabolic dysfunction and neurological disease with developmental and progressive features," which is incorporated by reference herein in its entirety.

BACKGROUND OF THE INVENTION

Genetic diseases commonly cause intellectual and developmental disability (~1-2% of the population) and carry an average lifetime cost per person of ~$1,000,000 in 2003 dollars, making them a substantial public health concern. Centers for Disease Control and Prevention, MMWR Morbidity & Mortality Weekly Report, 53, 57-59 (2004). Genetic diseases are a powerful resource for investigating mechanisms of human brain metabolism. Metabolic diseases can sometimes be amenable to treatments by dietary restrictions or supplements that can prevent intellectual disabilities when treated early in childhood. For phenylketonuria (PKU), early identification and dietary modification prevented developmental brain disease in hundreds of thousands of people. Camp et al., Mol. Genet. Metab., 112, 87-122 (2014). The prospect of newborn screening supported by genome-wide sequencing provides opportunities to intervene in metabolic developmental brain disease early in childhood. Therefore, there is a need in the medical art to determine which neurometabolic diseases can be amenable to interventions in early childhood.

These metabolic pathways and neuroprotective treatments can also pertain to a broad range of neurologic diseases. The inventors previously identified a novel human neurogenetic disorder caused by loss-of-function (LoF) mutations in the mitochondrial enzyme glutamate pyruvate transaminase 2 (GPT2), also known as alanine transaminase 2 (ALT2). Ouyang et al., Proc. Natl. Acad. Sci. U.S.A., 113, E5598-5607 (2016). GPT2 is a nuclear-encoded, mitochondrial enzyme enriched in the brain and upregulated during postnatal brain development. Ouyang et al., Proc. Natl. Acad. Sci. U.S.A., 113, E5598-5607 (2016). Several large families exhibit definitive LoF recessive mutations in GPT2 in patients with developmental and motor disabilities. In the Gpt2-null mouse brain, The inventors applied modern metabolic methods to begin defining the defective mechanisms. Many reports of families provide a high level of rigor for clinical genetics. The inventors' follow-up publication on GPT2 disease estimated the carrier frequency of deleterious mutations at 1/250 individuals of European ancestry, approximately ¼ as common as PKU mutations. In Pakistan, GPT2 disease is among the most common forms of recessive intellectual disability. Ouyang et al., Hum. Genet., 138, 1183-1200 (2019).

The later onset of spastic paraplegia in GPT2 disease suggests that motor disability is a target for preventive interventions after early or newborn diagnosis.

There remains a need in the art for therapeutic compounds to treat a deficiency in the glutamate pyruvate transaminase 2 (GPT2) enzyme.

SUMMARY OF THE INVENTION

The invention provides compounds and methods for treating a genetic disorder in childhood resulting from a mutation in the gene for the enzyme glutamate pyruvate transaminase 2 (GPT2). The mutation is a signature of metabolic defects.

In a first embodiment, the invention provides a method of treatment for this disorder by administering an alanine supplement to a child having the disorder.

In a second embodiment, the invention provides a method of treatment for this disorder by administering an anaplerotic supplement to a child having the disorder.

In a third embodiment, the anaplerotic supplement is triheptanoin. In a fourth embodiment, the anaplerotic supplement is a triheptanoin composition or a triheptanoin.

In a fifth embodiment, a combination of alanine and an anaplerotic supplement such as triheptanoin is administered to the child.

In a sixth embodiment, the invention provides a method of screening for a therapeutic compound for treating metabolic dysfunction or neurological disease with developmental and progressive features, using a Gpt2-null mouse model, such as disclosed in Ouyang et al., Proc. Natl. Acad. Sci. U.S.A., 113 (38), E5598-E5607 (Sep. 20, 2016).

In a seventh embodiment, the invention provides alanine for treating metabolic dysfunction or neurological disease with developmental and progressive features.

In an eighth embodiment, the invention provides an anaplerotic supplement, such as triheptanoin, for treating metabolic dysfunction or neurological disease with developmental and progressive features.

In a ninth embodiment, the invention provides a method of treating metabolic dysfunction or neurological disease with developmental and progressive features, comprising the step of administering a compound selected from the group consisting of alanine and an anaplerotic supplement, such as triheptanoin.

In a tenth embodiment, the invention provides a method of screening newborn humans for metabolic dysfunction or neurological disease with developmental and progressive features, comprising the step of screening the newborns for a Gpt2 mutation or a deficiency in the glutamate pyruvate transaminase 2 (GPT2) enzyme.

EXAMPLE 1 describes how to test mechanism-based treatments in the preclinical mouse model of GPT2 disease.

EXAMPLE 2 describes how to establish the infrastructure and collaborations, including with industry, to develop a clinical trial in patients.

BRIEF DESCRIPTION OF THE DRAWINGS

For illustration, some embodiments of the invention are shown in the drawings described below. The invention is not limited to the precise arrangements, dimensions, and instruments shown.

FIGS. 1A and 1B describe the effect of metabolomics on developing Gpt2-null mouse hippocampus reveals the temporal sequence of metabolic abnormalities. FIG. 1A is a set of Venn diagrams showing a PCA of metabolomics on the hippocampus at P0, P7, P14, or P18. Wild-type (green) and mutant (red) mice show distinct separation during postnatal development. FIG. 1B is a set of line graphs showing primary metabolites of the GPT2 reaction. Differences are seen earliest with alanine followed by glutamate. n=7 approximately per genotype. * p<0.05,  p<0.005, * p<0.0005.

FIGS. 2A-2C show that alanine synthesis and anaplerosis are defective in Gpt2-null cells. FIG. 2A is a bar graph and diagram of a chemical equation showing that alanine levels in wild-type and Gpt2-null cortical neurons in vitro. Flux analysis shows suppressed alanine labeling from glutamate. 15N (red) transferred from $[\alpha\text{-}^{15}N]$-glutamine, via $[\alpha\text{-}^{15}N]$-glutamate, to $[^{15}N]$-alanine. FIG. 2B is a graph showing reduced tricarboxylic acid (TCA) cycle intermediates by metabolomics in Gpt2-null mouse brain at P18. WT: n=6; Gpt2 Null: n=6. *=0.01<p<0.05, **=0.001<p<0.01. Red stars denote an FDR<0.05. FIG. 2C is a pair of bar graphs and a diagram of a chemical equation showing mass isotopologue distributions for malate (top) and citrate (bottom) after culture of wild-type and Gpt2-null mouse embryonic fibroblasts with unlabeled glucose and $[\text{U-}^{13}C]$-glutamine. The reduced direct transfer of radioisotope from glutamine to malate and citrate demonstrates suppressed anaplerosis in Gpt2-null cells. The schematic shows the generation of fully labeled a-ketoglutarate from $[\text{U-}^{13}C]$-glutamine via glutamate and subsequent generation of malate m+4, citrate m+4, and citrate m+5. Means±SDs for three cultures, with results shown for one representative experiment. *p<0.05,  p<0.01, * p<0.001.

FIGS. 3A-3E show that the Gpt2 mutation in mice recapitulates motor disability seen in patients. Syn1-Cre cKO mice phenocopy germline Gpt2-null mice, which is benefited by alanine supplementation. FIG. 3A shows weight curves. FIG. 3B shows survival curves of germline Gpt2-null mice with and without alanine, Syn1-Cre cKO Gpt2-mutant mice. The inventors also performed an Open Field Test showing mutant dragging hindlimbs. The inventors observed an aberrant hindlimb clasping reflex. FIG. 3C is a scatter plot showing wild-type and germline Gpt2-null and Syn1-Cre cKO mice, at P17, DigiGait analysis shows increased hindpaw angle. FIG. 3D is a plot showing the results of an Open Field Test, P18. FIG. 3E is a plot showing the results of a Wire Hang Test, P18. * p<0.05,  p<0.01, * p<0.001, **** p<0.0001.

FIG. 4 is a plot showing that Gpt2-null animals have reduced spinal cord length and upper motor neuron (UMN) tract volumes. The dots represent the average of three sections from the same animal. * p<0.05, ** p<0.01.

DETAILED DESCRIPTION OF THE INVENTION

Industrial Applicability

The disease progression in the postnatal period can be prevented by intervention, particularly in setting abnormalities of amino acid metabolism. Glutamate pyruvate transaminases have an essential function in several metabolic reactions, including amino acid metabolism, the urea cycle, and the tricarboxylic acid (Krebs) cycle, besides functions in neurotransmitter synthesis, both glutamate, and GABA. Glutamate is also a substrate for the synthesis of glutathione, a key element in the cellular machinery to protect against oxidative damage and cell death. The depletion of alanine levels is the strongest signal observed of the primary metabolites in the brain.

The goal is to conduct preclinical studies of the efficacy of mechanism-based treatments. Gpt2-null mice appear to recapitulate several key aspects of the neurologic disease, including undergrowth of brain and motor system dysfunction. To progress to clinical trials in patients, evaluate disease mechanisms and drug efficacy in vivo. The mouse is an ideal experimental system to meet these goals and address this problem.

Genes and cellular mechanisms are conserved between mice and humans. The mouse system offers additional powerful methods, including genetic manipulation. Many aspects of the mouse nervous system are comparable to those of other mammals, including primates. Published literature exists on the mouse nervous system and on developing neural circuits permitting a person having ordinary skill in the medical art to construct specific hypotheses. The mouse has the advantage of resources such as transgenic reporter lines.

The availability of transgenic mice has transformed the understanding of important proteins in the nervous system. Investigating mutant animals lacking Gpt2 provides important information that can be obtained no other way. Mice are thus the experimental system of choice. Conducting translational assays from the level of genetics to cell biology is the state-of-the-art approach to understanding the molecular basis of brain disease in well-powered investigations.

The inventors' laboratory was first to report multiple large families with definitive LoF recessive mutations in GPT2 in patients with developmental and motor disabilities. In a follow-up publication, the inventors enrolled other pedigrees. To date, over twenty families were published in the literature with GPT2 mutations. GPT2 disease represents a rare genetic condition. However, available internet-based technologies in worldwide communication allow for the engagement of families and treaters to facilitate clinical research into these important childhood disorders. While each of these childhood neurometabolic disorders may be individually rare, the possibilities of early intervention and treatment, preventing lifelong neurologic disability, can have a considerable positive impact on families and societies.

While GPT2 disease may be individually rare, if the inventors succeed in developing a treatment that prevents neurologic damage in children, this research can positively impact families and societies for generations. The research goal is even more urgent because the proposed treatments, alanine, and anaplerotic supplementation, can be implemented in patients near term. These agents are available for study in children.

Introduction to the Background of the Problem Presented

The GPT2 disease phenotype includes (1) postnatal microcephaly, reduced brain growth postnatally after normal head circumference at birth, which likely reflects abnormalities in developmental processes that underlie circuit development, such as axonal and dendrite growth and arborization, and synaptogenesis; (2) developmental and cognitive disability, generally in the moderate range; (3) epilepsy in a subset of patients; and (4) progressive spastic paraplegia. Hereditary spastic paraplegia (HSP) is a genetically heterogeneous condition, reflected by progressive motor disability affecting lower extremities, preferentially with an upper motor neuron (UMN) pattern, i.e., spasticity and hyperreflexia. See Blackstone, Annu. Rev. Neurosci., 35, 25-47 (2012); Fink, Semin. Neurol., 34, 293-305 (2014). In GPT2 disease, approximately 75% of patients have spastic paraplegia, with variable progression, including loss of ambulation. See Ouyang et al., Hum. Genet., 138, 1183-1200 (2019); Hengel et al., Clin. Genet., 94, 356-361 (2018).

Mitochondria and the tricarboxylic acid (TCA) cycle have a central function in biosynthetic mechanisms. Owen, Kalhan, & Hanson, J. Biol. Chem., 277, 30409-30412 (2002). GPT2 is one of two equilibrium transaminases that catalyze the reversible addition of an amino group from glutamate, the major excitatory neurotransmitter in the brain, to pyruvate, yielding alanine and a-ketoglutarate, a tricarboxylic acid cycle intermediate. Based on a mitochondrial targeting sequence, the subcellular localization of GPT2 is restricted to mitochondria, as opposed to the related GPT1, which is without a mitochondrial localization signal, localized to cytoplasms, and expressed at low levels in neurons. GPT2 is strongly upregulated during postnatal brain development, a period of rapid neuronal/axonal growth and synaptogenesis. Ouyang et al., Proc. Natl. Acad. Sci. U.S.A., 113, E5598-5607 (2016).

GPT2 is critical for neuronal and axonal growth. Motor disability emerges in patients with GPT2 disease and presents as hereditary spastic paraplegia. See Blackstone, Annu. Rev. Neurosci., 35, 25-47 (2012); Fink, Semin. Neurol., 34, 293-305 (2014). The pathophysiology of hereditary spastic paraplegia reflects defects in the growth or maintenance of long-range projection neurons (PNs). The preliminary data support a model wherein hereditary spastic paraplegia presents in GPT2 disease due to the requirement for GPT2 in neuronal and axonal growth. While hereditary spastic paraplegia is linked to over seventy genetic loci, genes implicated most often affect membrane trafficking or shaping of intracellular organelles. See Blackstone, Annu. Rev. Neurosci., 35, 25-47 (2012); Fink, Semin. Neurol., 34, 293-305 (2014). A few genes reflect mitochondrial or metabolic mechanisms. Knowledge of GPT2 function in motor disability can contribute to an understanding of pathogenesis in hereditary spastic paraplegia, given the limited genetic loci of the metabolic class.

A Gpt2-null mouse model recapitulates key aspects of diseases, such as hindlimb motor abnormalities, akin to spastic paraplegia seen in patients. Gpt2-null brains show a primary and severe deficiency in alanine synthesis. Alanine is one of the most commonly used amino acids for protein synthesis. GPT2 is required for alanine synthesis and anaplerosis, replenishing tricarboxylic acid cycle intermediates, during neuron growth.

The tricarboxylic acid cycle represents a major crossroad enabling fuel oxidation and building blocks for lipids and proteins. Owen, Kalhan, & Hanson, J. Biol. Chem., 277, 30409-30412 (2002). Gpt2-null brains demonstrate reduced tricarboxylic acid cycle intermediates and defective anaplerosis. Homeostatic regulation of anaplerosis and cataplerosis is crucial for tissue growth. Anaplerosis (filling up) is the process whereby tricarboxylic acid cycle intermediates are replenished. Anaplerosis is important during high biosynthetic demand when tricarboxylic acid cycle intermediates are consumed to synthesize macromolecules for cell growth, a process known as cataplerosis.

Use of Compositions of Matter for Treating GPT2 Disease

Based on the preliminary data, the inventors established potential treatment strategies for GPT2 disease, which currently has no treatment. The inventors showed two prominent neurometabolic abnormalities amenable to therapeutic interventions in the near term.

The inventors formed two overriding hypotheses (OH) regarding the function of GPT2. Absent GPT2, insufficient alanine leads to reduced growth (OH1). Impaired anaplerosis (OH2) leads to reduced tricarboxylic acid cycle intermediates, cataplerosis, and growth. The overriding hypothesis is that GPT2 is required for metabolic mechanisms central to neuronal and axonal growth during brain development, particularly in long projection neurons of the motor system.

These deficiencies can be treated with alanine and anaplerotic supplementation. During brain development, the biosynthetic needs of growing neurons are immense. This need is especially true for projection neurons with long axonal tracts such as those in the motor system. Gpt2 is essential for alanine synthesis (OH1) and is a critical neuronal anaplerotic enzyme in the brain (OH2) Ouyang et al., Proc. Natl. Acad. Sci. U.S.A., 113, E5598-5607 (2016).

Overriding hypothesis 1 (OH1). Absent GPT2, alanine changes to an essential amino acid in brains, and limited neuronal alanine impede neuronal and axonal growth. Thus, the first therapeutic strategy that the inventors are testing is dietary alanine supplementation. Alanine is commercially available as a nutritional supplement and crosses the blood-brain barrier. See Oldendorf, Am. J. Physiol., 221, 1629-1639 (1971); O'Kane et al., Am. J. Physiol. Endocrinol. Metab., 287, E622-629 (2004). The preliminary data in the mouse model of Gpt2 disease demonstrate that alanine supplementation in development partially ameliorates the phenotype.

Overriding hypothesis 2 (OH2): GPT2 deficiency causes impaired neuronal anaplerosis, impeding neuronal growth, particularly long axons of projection neurons, such as upper motor neurons involved in spastic paraplegia. Thus, the second therapeutic strategies to test are anaplerotic therapies.

Low alanine and low tricarboxylic acid cycle intermediates in GPT2 disease: Extensive data from neuroscience research and cancer research demonstrate a central function for Gpt2 in neuronal growth. See Kim et al. Oncogene, 38, 4729-4738 (2019); Smith et al., Cell. Rep., 17, 821-836 (2016); and Hao et al., Nature Commun., 7, 11971 (2016).

The inventors conducted metabolomics studies on acutely isolated hippocampus across development. See FIG. 1A. Using principal component analysis (PCA), the inventors observed separation of mutant and wild-type (WT) metabolomes during postnatal development, the time of upregulation of Gpt2 enzyme. Among the very few early differences (at P0) are perturbations in alanine, which, after an initial elevation, then shows a strong decline, followed by decreases in glutamate across postnatal development. See FIG. 1B.

The rigor of this prior research was based on the synergy of two complementary metabolism methods: metabolomics and direct isotope tracing. Regarding alanine synthesis, to complement the low alanine result in metabolomics, FIG. 2A shows a profound decrease of flux from glutamate to alanine in Gpt2-null neurons. Human patients with GPT2 disease show low alanine in the blood. Celis et al., Loss of function mutation in glutamic pyruvate transaminase 2 (GPT2) cause developmental encephalopathy. J. Inherit. Metab. Dis., 38, 941-948 (2015).

The inventors observed a strong decrease of tricarboxylic acid cycle intermediates in the Gpt2-null brain using metabolomics. See FIG. 2B. The inventors also observed a strongly decreased flux from glutamine into tricarboxylic acid intermediates by direct isotope labeling assays. FIG. 2C. The inventors also observed an increased flux of glucose into tricarboxylic acid cycle intermediates, i.e., increased glycolysis, akin to a neuronal Warburg effect. Ouyang et al., Proc. Natl. Acad. Sci. U.S.A., 113, E5598-5607 (2016).

Improvements

The inventors are pursuing the treatment of the mouse model with alanine+/−triheptanoin with some success.

Definitions

For convenience, the meaning of some terms and phrases used in the specification, examples, and appended claims, are listed below. Unless stated otherwise or implicit from context, these terms and phrases have the meanings below. These definitions are to aid in describing particular embodiments and are not intended to limit the claimed invention. Unless otherwise defined, all technical and scientific terms have the same meaning as commonly understood by a person having ordinary skill in the medical art t. For any apparent discrepancy between the meaning of a term in the art and a definition provided in this specification, the meaning provided in this specification shall prevail.

A or An means at least one or one or more unless the context shows otherwise.

About means that the recited numerical value is approximate. Slight variations would not significantly affect the practice of the disclosed embodiments. Where a numerical value is used unless shown otherwise by the context, about means the numerical value can vary by +10% and remain within the scope of the disclosed embodiments.

Anaplerotic has the biochemical art-recognized meaning of a compound that affects chemical reactions that form intermediates of a metabolic pathway. Examples of such are found in the citric acid cycle (TCA cycle). In the normal function of this cycle for respiration, concentrations of tricarboxylic acid intermediates remain constant; however, many biosynthetic reactions also use these molecules as a substrate. Anaplerosis is the act of replenishing citric acid cycle intermediates that were extracted for biosynthesis (in what are called anaplerotic reactions).

Carrier has the medical chemical art-recognized meaning of a diluent, adjuvant, or excipient with which a compound is administered in a composition.

Compound has the medical chemical art-recognized meaning of all stereoisomers, tautomers, isotopes, and polymorphs of the compounds.

Comprising (and any form of comprising, such as Comprise, Comprises, and Comprised), Having (and any form of Having, such as Have and Has), Including (and any form of Including, such as Includes and Include), or Containing (and any form of Containing, such as Contains and Contain), are inclusive and open-ended and include the options following the terms, and do not exclude additional, unrecited elements or method steps.

Contacting has the medical chemical art-recognized meaning of bringing together two compounds, molecules, or entities in an in vitro system or an in vivo system.

Glutamate pyruvate transaminase 2 (GPT2) has the biochemical art-recognized meaning of an enzyme with an important function in various metabolic reactions, including amino acid metabolism, the urea cycle, and the tricarboxylic acid cycle, besides functions in neurotransmitter (both glutamate and GABA) synthesis. Glutamate is also a substrate for the synthesis of glutathione, a key element in the cellular machinery to protect against oxidative damage and cell death.

Individual, Subject, and Patient used interchangeably means any animal. In some embodiments, the mammal is a human.

Mammal has the medical chemical art-recognized meaning and includes rodents, monkeys, and humans. In some embodiments, the mammal is a human.

Pharmaceutically acceptable salts include but are not limited to salts of acidic or basic groups. Basic compounds can form a wide variety of salts with various inorganic and organic acids. Compounds that include an amino moiety can form pharmaceutically acceptable salts with various amino acids. Acidic compounds can form base salts with different pharmacologically acceptable cations. Salts include quaternary ammonium salts of the compounds described, where the compounds have one or more tertiary amine moiety.

Pharmaceutically acceptable has the medical chemical art-recognized meaning that the compounds, materials, compositions, or dosage forms are within the scope of sound medical judgment and are suitable for contact with tissues of humans and other animals. The pharmaceutically acceptable compounds, materials, compositions, or dosage forms result in no persistent detrimental effect on the subject or the general health of the treated subject. Still, transient effects, such as minor irritation or a stinging sensation, are common with the administration of medicament and follow the composition, formulation, or ingredient, e.g., excipient, in question. Guidance about what is pharmaceutically acceptable is provided by comparable compounds, materials, compositions, or dosage forms in the US Pharmacopeia or another generally recognized pharmacopeia for use in animals, particularly in humans.

Prevention or preventing has the medical chemical art-recognized meaning of reducing the risk of acquiring a disease, condition, or disorder.

Therapeutically Effective amount has the medical chemical art-recognized meaning of the amount of active compound or pharmaceutical agent that elicits the biological or medicinal response sought in a tissue, system, animal, individual, or human by a researcher, veterinarian, medical doctor, or another clinician. The therapeutic effect depends upon the disorder being treated or the biological effect desired. The therapeutic effect can be a decrease in the severity of symptoms associated with the disorder or inhibition (partial or complete) of progression of the disorder, or improved treatment, healing, prevention or elimination of a disorder, or side-effects. The amount needed to elicit the therapeutic response can be based on, for example, the age, health, size, and sex of the subject. Optimal amounts can also be determined based on monitoring of the subject's response to treatment.

Treat, Treated, or Treating has the medical chemical art-recognized meaning of both treatment and prophylactic or preventive measures wherein the object is to prevent or slow down (lessen) an undesired physiological condition, disorder or disease, or obtain beneficial or desired clinical results. Beneficial or desired clinical results include, but are not limited to, alleviation of symptoms; diminishment of the extent of the condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of the condition, disorder or disease. Treatment includes eliciting a clinically significant response, optionally without excessive levels of side effects. Treatment also includes prolonging survival as compared to expected survival if not receiving treatment.

Triheptanoin has the biochemical art-recognized definition of triglyceride composed of three seven-carbon (C7:0) fatty acids. Triheptanoate is a tasteless oil. Triheptanoin is cleaved into heptanoate and subsequently metabolized to propionyl-CoA and then succinyl-CoA, which are anaplerotic. Triheptanoin is used clinically in humans to treat inherited metabolic diseases, such as pyruvate carboxylase deficiency and carnitine palmitoyltransferase II deficiency. This fatty acid also increases the efficacy of the ketogenic diet as a treatment for epilepsy. Triheptanoin crosses the blood-brain barrier. In preclinical studies, triheptanoin has antiseizure effects. See Willis et al. (2010). Neurobiol. Dis., 40, 565-572 and Hadera et al., J. Neurochem., 129, 107-119 (2014). Triheptanoin has been used in clinical trials for childhood neurometabolic disorders, e.g., NCT01379625 and NCT01993186, where the drug is well tolerated. Vockley et al., Mol. Genet. Metab., 120, 370-377 (2017). Ultragenyx produces the anaplerotic drug triheptanoin [UX007]. Triheptanoin is provided free-of-charge from Ultragenyx, and the formulations are generated by Envigo, which is fed to the breeding pairs, pregnant mothers, and pups. Dosing methods and tolerability are described in the published literature about using triheptanoin in mice by Ultragenyx. See Willis et al., Neurobiol. Dis., 40, 565-572 (2010) and Hadera et al., J. Neurochem., 129, 107-119 (2014). In terms of dose, 30% by caloric intake trihepatnoin in the total chow is added to an amino acid-defined diet. As Gpt2-null pups survive, they continue having the triheptanoin diet for up to twelve months, depending on the assay. Ultragenyx is a clinical-stage biotechnology company with a commitment to conducting therapeutic trials in children with genetic disorders.

The terms Comprise and Comprising should be interpreted as referring to elements, components, or steps in a non-exclusive manner, indicating that the referenced elements, components, or steps may be present, used, or combined with other elements, components, or steps. The singular terms a, an, and the include plural referents unless context shows otherwise. Similarly, the word or should cover and unless the context shows otherwise. The abbreviation e.g. is used to show a non-limiting example and is synonymous with the term for example.

When a range of values is provided, each intervening value, to the tenth of the unit of the lower limit, unless the context dictates otherwise, between the upper and lower limit of that range and any other stated or intervening value in that range of values.

Guidance from Materials and Methods

A person having ordinary skill in the medical art can use these materials and methods as guidance to predictable results when making and using the invention.

Vertebrate animal assays. The assays use a wild-type mouse line and a genetically modified mouse line (i.e., germline Gpt2-null line). A person having ordinary skill in the biomedical art can perform these assays following the procedures in protocol 18-11-0002, approved by the Brown University Institutional Animal Care and Use Committee (IACUC). All animals used in assays described in this specification were housed at the Brown University Animal Care Facility.

Mice with the germline-null mutation of Gpt2 were described by Ouyang et al., Proc. Natl. Acad. Sci. U.S.A., 113, E5598-5607 (2016). The CrymGFP mouse is available from the Mutant Mouse Resource & Research Centers (Stock No.: 012003-UCD).

All assays are performed blind to genotype to reduce bias and enhance rigor. Tail snips for genotyping are acquired early, from 1-3-day-old and up to 10-day-old pups, using a sterile scalpel. As small a piece of the tail as possible is removed, generally <3 mm. Animals to be used in the investigation are indicated to investigators who are blind to genotype. Breeding pairs are maintained from ages six-eight weeks to six months. The inventors do not breed aged mice, particularly males, due to the risk of new germline mutations. The infertility factor is calculated: 15% of C57BL/6J inbred background strain matings are infertile and 10% factor for dystocia and other non-breeding related issues, hence the extra 25% of the calculated ideal mouse numbers needed.

Assays for motor circuitry development and function in Gpt2-null mice in vivo. In EXAMPLE 1, The inventors examine upper motor neurons, lower motor neurons, and motor behavior in two in vivo paradigms using germline Gpt2-null mice and littermate controls with and without dietary treatments. Gpt2-null mice survive until P18-P28. TABLE 1 shows predicted results for each of the areas of assessment: motor behavior, neuropathology, or electrophysiology.

TABLE 1

Assays and predictions for in vivo studies and preclinical treatment

| Phenotype/Assay | Predicted Results |
| --- | --- |
| Motor Behavior. DigiGait, Open Field, Rotarod, Wire Hang | Abnormal gait due to hindlimb defects resulting from the undergrowth of long-range UMN PNs. Rescue of motor behavior with alanine, triheptanoin, and greatest improvement with combined treatment. |
| Neuropathology/Histology, IHC, Transgenic labeling | Long-range UMN PNs more affected than LMNs, smaller UMN soma in mutant cortex, dying UMN axons in mutant spinal cord, decreased UMN axon numbers, late cell death in UMNs, increased ROS. Rescue of neuropathology with alanine, triheptanoin, and greatest improvement with combined treatment. |
| Electrophysiology. EMG, Nerve conductance, MEPPs, Muscle force transducer | Slower axonal conductance of most distal LMNs in mutant, reduced frequency and amplitude of MEPPs in mutant, reduced muscle strength in mutant. Rescue of electrophysiology defects with alanine, triheptanoin, and greatest improvement with combined treatment. |

Motor behavior: The inventors use Open Field Test, Hindlimb Clasping Reflex, Rotarod, and Wire Hang Test (FIG. 3G). The inventors also use DigiGait, for computer-automated video analysis of gait (FIG. 3E), which permits an information-rich and highly sensitive investigation of small animal, natural gait. DigiGait has been applied to models of neurological disorders, including amyotrophic lateral sclerosis (ALS) and hereditary spastic paraplegia. See Connell & Reid, PLOS One, 11, e0152413 (2016). Analysis involves computer-assisted quantification of paw position and angle, stride length, speed, forepaw and hindpaw base width, and paw overlap. Mice are tested recurrently after P15 to assess the progression of worsening gait.

Neuropathology: The inventors examine neuropathological and immunohistochemical (IHC) defects in upper motor neurons and lower motor neurons in Gpt2-null mice, before the emergence of pathologies (P12) until shortly before death (P18-P28), using methods published by Valdez et al., Proc. Natl. Acad. Sci. U.S.A., 107, 14863-14868 (2010); Sugita et al., Skelet. Muscle 6, 31 (2016); and Maxwell et al., Aging Cell, 17 (2018). The inventors predict defects in axons in upper motor neurons more than lower motor neurons. Upper motor neurons can derive from corticospinal tract (CST) neurons. However, the inventors also investigate the rubrospinal tract (RST) neurons, which in a mouse can compensate for early developmental defects in the corticospinal tract. Fink & Cafferty, Neurotherapeutics 13, 370-381 (2016).

Upper motor neurons and descending axonal tracts: The inventors use state-of-the-art microscopy to examine corticospinal tract neurons in layer 5 cortex and upper motor neurons in the red nucleus to assess their health. The inventors do not anticipate evidence of prominent cell loss, as this is rarely seen in mouse models of spastic paraplegia. Genc, Gozutok, & Ozdinler, Int. J. Mol. Sci. 20 (2019). The inventors predict these large neurons are smaller in size. Layer 5 of the cortex is identified via depth, density of large pyramidal somata, layer-specific makers (CTIP2 and mucrystallin, Crym) [see Arlotta et al., Neuron, 45, 207-221 (2005); Ozdinler et al., J. Neurosci., 31, 4166-4177 (2011)], and transgenic reporter lines, such as Crym-GFP. See Fink, Strittmatter, & Cafferty, J. Neurosci., 35, 15403-15418 (2015). Neurons of the red nucleus are identified by immunohistochemistry for C1QL2 and vGluT2. Liang, Paxinos, & Watson, Brain Struct. Funct., 217, 221-232 (2012). The inventors examine neuronal health of corticospinal tract and rubrospinal tract neurons utilizing Fluoro-Jade B. See Schmued & Hopkins, Brain Res., 874, 123-130 (2000) and Yamaguchi & Shen, Histological analysis of neurodegeneration in the mouse brain. Methods Mol. Biol., 1004, 91-113 (2013). Immunohistochemistry for Caspase 3, increases in ubiquitinated protein (anti-Ub), reactive microglia, e.g., Iba1, CD68, and reactive astrocytes, e.g., GFAP; and detection of increased reactive oxygen species (ROS).

Spinal cord: The inventors examine cross-sectional pathology of the spinal cord at three levels, cervical, thoracic, and lumbar. These data demonstrate reduced cross-sectional volume and length of spinal cord over reduction in animal size. See FIG. 4. Synapse numbers from descending upper motor neurons are assessed by staining for vGlut2 and SV2, using vGlut1-positive synapses from peripheral sensory nerves as controls. For upper motor neuron axons, the inventors use immunohistochemistry for myelin basic protein and axonal markers (silver stain, tau, tubulin, PKC-gamma) and reporter lines such as Crym-GFP. See Fink, Strittmatter, & Cafferty, J. Neurosci., 35, 15403-15418 (2015).

Lower motor neuron and neuromuscular junctions: Stainings to assess size, health, and numbers of lower motor neurons are as above for upper motor neurons: Nissl, NeuN, Fluoro-Jade B, Caspase 3, ROS, microglia, and astrocytosis. However, for lower motor neurons, the inventors stain for ChAT, Isl1/2, and HB9. Lower motor neuron axons are assessed by immunohistochemistry on cross-sections of ventral roots, comparing the relative thickness of myelin sheath (S100B) to axonal caliber (neurofilament). The inventors predict the reduction of axon caliber with most distal, long motor nerves, i.e., tibial nerve. To examine neuromuscular junctions, the inventors stain for synaptotagmin-2 for motor axon nerve endings and nicotinic acetylcholine receptors (nAChRs) for post-synapses. The inventors assess neuromuscular junctions for degeneration features, including loss of innervating motor axons, fragmentation, and decreased density of nAChRs.

Electrophysiology: The inventors are conducting electrophysiology assays of muscle and electromyography (EMG) of the sciatic nerve and distal nerves, as published by Sugita et al., Skelet. Muscle 6, 31 (2016) and Higashimori et al., Muscle Nerve, 31, 610-620 (2005). Reduced nerve conduction velocities in distal motor nerves should occur. To examine the functional output of lower motor neurons, the inventors measure synaptic transmission at neuromuscular junctions using muscle intracellular recordings of endplate potentials (EPPs) and miniature endplate potentials (MEPPs). The inventors measure muscle contractions (strength and fatigue) using a muscle force transducer.

Rescue of motor phenotype in vivo with dietary modifications. Synthesis of alanine in the brain is prominently deficient in Gpt2-null animals. An overriding hypothesis (OH1) is that, in the absence of GPT2, alanine changes from a non-essential amino acid to an essential amino acid in neurons, and neuronal alanine deficiency impedes protein synthesis and neuronal growth. The inventors determined there is an anaplerotic defect in Gpt2-null brains (OH2). See FIGS. 2A-2C. The inventors are attempting to rescue animal survival, weight gain, and health of the motor system by alanine supplementation, anaplerotic supplementation, and the combination. The inventors demonstrated in preliminary work that alanine supplementation improves the survival of the germline Gpt2-null animal, i.e., mutant animals survive. See FIG. 3B. The inventors are testing the extent to which other phenotypic aspects, particularly related to motor defects, are ameliorated by alanine supplementation over time with and without anaplerotic supplementation. The inventors also investigate the requirement for exogenous dietary alanine by removing alanine from the diet of Gpt2-null animals.

Alanine supplementation: Littermate germline Gpt2-null and wild-type animals are fed either high-alanine diet (5% by weight), alanine-deprived diet (0%), or standard chow (1.2%). The formulations generated by Envigo are fed to breeding pairs, pregnant mothers, and pups, based on prior studies by Battaglia & Regnault, Placenta, 22, 145-161 (2001). Food is provided ad libitum. Therefore, newborn Gpt2-mutant pups are receiving the diet throughout gestation and from birth onward. High-alanine diets led to the survival of Gpt2-null animals past P30, which is never seen for mutant mice on a standard diet. See FIG. 3B. The inventors measured alanine in peripheral blood and brain tissue by metabolomics. The inventors also test animal weight and the weight of food remaining. Alternatively, the mice can consume the requisite diet by oral gavage of food. The inventors are also testing the ongoing requirement for alanine by withdrawing alanine from the diet at P40 and beyond (i.e., alanine-free diet) in surviving germline Gpt2-null animals. The mice could require ongoing alanine supplementation. Gpt2-mutant animals could exhibit new phenotypes, i.e., failures in weight gain, degeneration of motor circuitry, and death after alanine withdrawal.

Anaplerotic supplementation. In germline Gpt2-null littermate pairs, the inventors test anaplerotic supplementation through the addition of triheptanoin to the food, as has been published by Park et al., PLOS One, 9, e109527 (2014); and Francis, Markov, & Leone, J. Inherit. Metab. Dis., 37, 369-381 (2014). Animals are fed either a triheptanoin-supplemented diet or standard chow.

Combination high-alanine and anaplerotic supplementation: The inventors also test the combination of alanine and anaplerotic supplementation, a diet prepared by Envigo. Gpt2-mutant animals are compared across these conditions: alanine alone, triheptanoin alone, combination, and standard chow.

Minimization of pain and distress. All animal procedures comply with Brown University IACUC guidelines. The mice are housed in a controlled environment in the Animal Care Facility at Brown University. The mice receive daily care from laboratory personnel. The mice are routinely monitored by a veterinarian and staff from the Brown University Center for Animal Research and Education (CARE). The mice do not experience significant pain or discomfort during any of the described assays.

Adult mice are sacrificed with pentobarbital injection or treated with carbon dioxide before rapid decapitation for tissue harvest. In performing minor surgeries for muscle physiology, muscle force test, and EMG studies, mice receive appropriate anesthesia before surgeries and during the assays. Anesthetized mice are placed on a warm-water heating pad. Body temperatures are maintained at 37° C. during recordings. The mice also receive post-surgery analgesia and care by trained personnel and CARE staff. Animals used for experimentation are monitored daily by laboratory personnel. Any clinical signs of animal distress, pain, or poor body condition are reported. A veterinarian is consulted as necessary to determine the appropriate actions to take. The personnel are extensively trained and certified by veterinarians on the CARE staff for all euthanasia procedures. The methods follow the Guiding Principles in the Care and Use of Animals, as approved by the Council of the American Physiological Society. The Brown University Animal Care Facility is accredited by the American Association for the Accreditation of Laboratory Animal Care and meets NIH guidelines in the Guide for Care and Use of Laboratory Animals. See, National Research Council of the National Academies (2011) and Guide for the Care and Use of Laboratory Animals, 8th edition (Washington, DC: The National Academies Press).

Human subjects involvement, characteristics, and design. These investigations involve establishing and maintaining an international cohort of patients with GPT2 disease with clinical collaborators to prepare for a clinical trial. The protocol under which this human subjects research is to be conducted has been approved by the Lifespan Institutional Review Board (IRB) and is active (Protocol No.: 640453). The investigation was reviewed to 45 C.F.R. 46.404 Subpart D-Children and is considered minimal risk.

The overall goal is to understand the genetic causes, classifications, and natural history of developmental disorders and related neurologic diseases. The specific focus of studies in this grant application is GPT2 disease, an autosomal recessive genetic disorder with early-onset. Common features of affected individuals with GPT2 disease include postnatal undergrowth of the brain, i.e., microcephaly, developmental delay, intellectual disability, epilepsy, and hereditary spastic paraplegia. Individuals with GPT2 mutations, and biologically related controls, are enrolled based on outreach to genetic diagnostic clinics and through contacts with families with GPT2 disease. Blood sample collection is currently approved. These studies extend to blood collection for metabolomics-based analysis to pilot potential biomarkers of disease.

GPT2 disease is an autosomal recessive genetic disorder with early-onset. Individuals are recruited across the lifespan, from approximate age six months through adulthood. This recruitment allows for clinical information and biological samples, e.g., blood samples, to be obtained from individuals at various stages of this progressive disorder. No individuals are excluded based on sex, race, ethnicity, or age alone.

The primary enrollment site is Emma Pendleton Bradley Hospital in East Providence, RI, USA. When possible, patients are brought to this site to participate in research. Bradley Hospital is one of the nation's largest, free-standing tertiary care hospitals for childhood neurodevelopmental disorders.

Eligibility criteria: Affected participants are individuals aged six months or older who meet DSM-5 criteria for Autism Spectrum Disorder or Intellectual Disability in their life (probands). Family members, i.e., parents and siblings, of affected individuals are recruited whether or not they ever met the criteria for any of the above disorders. Exclusion criteria include known environmental causes for Autism Spectrum Disorder or Intellectual Disability, e.g., birth trauma. If participating in the Rare Genetics Registry portion of the overarching protocol governing the investigation, participants must have received confirmatory clinical genetic testing indicating a mutation in a gene of interest (i.e., GPT2), the parent or legal guardian must have met with a clinician in this regard, and the affected participant must have an active clinician.

Procedures and materials. The overall investigation involves three steps: (a) Baseline medical record review and clinical assessments (remotely or in-person). (b) Confirmation of genetic mutations of interest and interview of treating clinicians. (c) Longitudinal follow-up and assessment to define the natural history of symptoms. Participants, both affected and biologically-related unaffected individuals, are enrolled following approved informed consent and assent procedures. Medical histories and records are obtained. Standardized clinical instruments are used for collecting data. Information is also requested to create a Global Unique Identifier (GUID) for each study participant. Blood samples are collected by peripheral blood draw from affected individuals and biologically related control individuals. Families can be re-contacted to obtain additional information or biological samples. After a review of medical records, relevant clinical treaters are interviewed. Participants are assigned a Global Unique Identifier. All data are keyed by a de-identified code. The obtained clinical data is stored in a password-protected database or a locked filing cabinet in a locked clinical room. Individuals involved in the investigation remain confidential and are identified by coded numbers to protect their identities. Personnel with access include only those approved by the IRB and who have credentialing in methods of human subjects research and HIPAA. The collected blood samples are used for DNA preparations and reprogramming to generate iPSCs.

Potential risks: The investigation has no more than minimal risks. There is no physical discomfort associated with the clinical assessments and measures. There is a small risk associated with venipuncture in obtaining a blood sample, e.g., pain, bruising, infection, or nerve damage. Appropriate precautions are taken in obtaining blood samples, and blood draws are performed by credentialed phlebotomists.

Because affected participants have a serious medical condition, a family's emotional investment in the research can be high. The development of unrealistic expectations for the outcome of the study is a potential risk. Emotional and psychological risks are also possible with research studies involving collecting medical information and genetic testing. Parents or legal guardians providing consent for affected participants are advised of the research limits and the likelihood of specific outcomes.

There is a risk of inadvertent disclosure of protected health information (PHI). Staff try to protect confidential information by following standard precautions and study procedures for de-identifying, recording, and securely storing all study information. In publishing results, names or personally identifiable information are not used. A participant could be recognized because of the rarity of GPT2 disease or based on a participant's rare DNA sequence change. Still, it would be very difficult to identify an individual based on such published data. Still, it is a potential risk, particularly with identification by a parent or family member who is aware of some medical information in advance. Parents or legal guardians of participants are advised to obtain informed consent. Participants always have an active treater who serves as a contact for staff and manages medical treatment.

The risk of misuse of a participant's genetic information also exists. The risk that a participant's genetic or personal information could be released inadvertently is small. Also, there are laws in place to help prevent most forms of discrimination against an individual based on his/her genetic information, i.e., Genetic Information Nondiscrimination Act of 2008 (GINA). Participants or parents or legal guardians of participants are made aware of this information in obtaining informed consent.

Informed consent and assent. Upon expressing interest in studies covered by the overall protocol, families are provided with the consent documents for review, discussion with staff, and signature. At the discretion of the parent or legal guardian and considering an affected participant's ability to understand the investigation, time is given to discuss the investigation directly with the participant and obtain assent. Informed consent is obtained directly for participants 18 years old or older and mentally capable of providing consent. Informed consent is obtained from a parent or guardian for children <18 years old, assent from the child when appropriate, and for individuals eighteen years old or older but decisionally impaired. Plans for data and biospecimen sharing are made explicit in the informed consent documents according to NIH guidelines.

Protections against risk. A subset of the intake forms and medical records include PHI. These materials are maintained in a locked cabinet in a locked office within a designated area that can be accessed only by a restricted number of trained members of the research team. Otherwise, data are stored and analyzed in coded form so that no person can be individually identified. Access to this dataset is restricted, password-protected, and maintained in a secure Lifespan-based system. Before any information, biosamples, or cell lines relating to this investigation are shared with outside investigators or sent to a biorepository, identifying information is replaced with a code number (i.e., GUID).

Participants or parents, or legal guardians of participants are advised that results of this investigation may be published in the medical literature. Names or personally identifiable information are not used when publishing results. Most of the data would be presented as aggregate/group data. A subset of data may show results linked to a specific genetic change. A participant could be recognized by family members or individuals knowledgeable about the genetic change of the participant because of the rarity of GPT2 disease or based on a participant's rare DNA sequence change. Still, it would be very difficult to identify an individual based on such published data without prior knowledge of the genetic change. Accordingly, participants or the parents or legal guardians of participants are advised in obtaining informed consent. Participants or parents or legal guardians providing consent for participants are advised of the research limits and the likelihood of specific outcomes.

Vulnerable subjects. GPT2 disease is a neurogenetic disorder with generally moderate intellectual disability as one characteristic feature. In particular, with genetic testing, a diagnosis can be made in early childhood, e.g., one-two years old. By nature of the disorder, the target population is recognized as a vulnerable population per federal guidelines. Parents or legal guardians provide consent for participants who are considered to be a minor (<18 years of age). Participants older than age 8 give assent, if they have sufficient mental capacity, by signing the consent form. Adult participants with GPT2 disease generally have their legal guardians and must have an identified guardian to be eligible for enrollment. The IRB-approved investigation is minimal risk and was reviewed to 45 C.F.R. 46.404 Subpart D-Children.

Potential benefits of the proposed research to research participants and others. The overall IRB-approved investigation is a research study, not a clinical service or a treatment study designed to benefit participants directly. For aspects of the investigation focusing on GPT2 disease, the research team may provide general information about the gene and associated symptoms to parents or legal guardians of participants or a participant's doctor with approval. The provision of general information about GPT2 disease may be of benefit to families. The research team cannot provide specific medical advice or treatment to participating families. This advice is clarified to families in the consent form and during the review of the consent form. Instead, families must rely on their local doctors for the treatment of their children. Therefore, there is no guarantee of benefits to participants or their families. There is no provision for compensation to participants or families for any commercial products derived from research results relating to the investigation. Participation in the investigation increases the available information for families and doctors regarding the effects of changes in the GPT2 gene on cellular function and potential treatments for GPT2 disease. Participation in the investigation can benefit the community of affected families, the medical field, and society. However, parents or legal guardians of affected participants are cautioned that the investigation is unlikely to be of direct benefit to their children or their families. Considering the potential benefits of the knowledge gained in advancing the field and treatment regimens, the minimal risks to which participants are exposed by way of the investigation procedures are reasonable. Dr. Morrow maintains ongoing contact with families and is available to families to provide updates regarding the progress of the research and information regarding GPT2 disease and new studies. The program has an IRB-compliant mechanism to help families with GPT2 disease connect with each other, which is generally positively embraced by families.

Importance of the knowledge to be gained. Participation in the investigation increases the available information for families and doctors regarding mutations in GPT2, phenotypes of GPT2 disease, and potential therapeutics. Participation in the exploration could benefit treatment development, the community of affected families, the medical field, and society in general.

Enrollment. The specific focus of the exploration is GPT2 disease, an autosomal recessive genetic disorder affecting males and females. Individuals with GPT2 mutations, and biologically related controls, are drawn from a larger group of study participants who have undergone genetic testing and assessments for autism and related developmental disorders. Both males and females are included in participation and can be included in the investigation as an affected individual or as the biologically related control of an affected individual. No racial or ethnic group is excluded from participation, and efforts are made to ascertain a diverse sample. GPT2 disease is a relatively rare genetic disorder, and participants are recruited from a broad referral population that includes diverse populations. To the extent possible, efforts are made to recruit broadly, regardless of sex, race, or ethnicity.

The following EXAMPLES are provided to illustrate the invention and shall not limit the scope of the invention.

Example 1

Define the Efficacy of Alanine, Triheptanoin, and Combination Treatments in Ameliorating Motor Phenotypes in Gpt2-Null Mice The purpose of this EXAMPLE is to define the efficacy of alanine, triheptanoin, and combination treatments in ameliorating motor phenotypes in Gpt2-null mice. Patients with null mutations in GPT2 present with progressive spastic paraplegia, a length-dependent axonopathy. Gpt2-null mice recapitulate hindlimb motor defect. The working hypothesis is that loss of Gpt2 leads to deficiencies in alanine synthesis and anaplerosis that cause defective neuronal/axonal growth in motor circuitry. The inventors are testing in vivo by defining the therapeutic efficacy of alanine supplementation, anaplerotic supplementation, and combination therapies on motor symptoms in Gpt2null mice.

Patients with null mutations in GPT2 present with spastic paraplegia, presumably due to upper motor neuron length-dependent axonopathy affecting lower limbs. The preliminary data demonstrate that Gpt2-null mice recapitulate motor defects. See FIGS. 3A-3G. The objective is to rescue axonal growth in vivo and motor behavior with supplementation of alanine or anaplerotic therapies. The working hypothesis is that loss of Gpt2 leads to defective neuronal alanine synthesis (OH1) and defective neuronal anaplerosis (OH2). These metabolic defects cause impairments in neuronal growth, particularly in projection neurons. This approach investigates neuronal/axonal growth in motor circuitry in Gpt2-null mice in vivo. The inventors test dietary supplementation of alanine or anaplerotic agents. The rationale is that determining the efficacy of treatments provides a clear path to therapeutics in patients.

Preliminary Data. The inventors developed the first mouse germline null and floxed, conditional knockout (cKO) allele for GPT2 diseases. In both germline and cKOs, these data support a function for Gpt2 in neuronal and axonal growth of long-range projection neurons governing motor behavior. Conditional deletion of Gpt2 in neurons alone by driving Cre recombinase using a Synapsin 1 promoter, i.e., Syn1-Cre (see Genes Dev 15, 859-876 (2001)), phenocopies germline Gpt2 deletion, indicating a critical, cell-autonomous Gpt2 function in differentiating neurons. Germline Gpt2-null and Syn1-Cre cKO mice have identical growth, survival, and motor behavior defects. See FIGS. 3A-3G. Mice lacking Gpt2 mature normally until approximately P16, when the growth of the mice decline relative to littermate controls. See FIG. 3A. Gpt2 protein expression and Gpt2 activity are strongly upregulated in this postnatal period. Ouyang et al., Proc. Natl. Acad. Sci. U.S.A., 113, E5598-5607 (2016). Mice die between P18-28. See FIG. 3B. These deaths may be due to abnormal projection neuron growth leading to impaired swallowing or movement. Akin to the human hereditary spastic paraplegia phenotype, both germline Gpt2-null and Syn1-Cre cKO mice develop identical hindlimb motor phenotypes. At approximately P19, mice begin to drag hindlimbs when walking. The mice demonstrate a hindlimb clasping defect. On computer-automated video analysis of gait (DigiGait), animals show hindlimb motor defects, including a larger paw angle, reflecting hindlimb weaknesses. The timing of these motor defects shows developmental undergrowth of upper motor neuron spinal axons. The inventors observe the undergrowth of the spinal cord and upper motor neuron spinal axons. See FIG. 4. The inventors also test the full motor circuitry, including lower motor neuron (LMN) and the neuromuscular junction (NMJ).

The preliminary data demonstrated a deficiency in alanine synthesis in the Gpt2-null brain. The inventors began to test the therapeutic efficacy of supplementation of alanine in the diet of pregnant and lactating mothers and Gpt2-null pups. In preliminary assays, supplemental dietary alanine results in survival of germline Gpt2-null pups, freely feeding, beyond weaning (36.7% on alanine vs. 0% on standard chow, $p<0.0001$, log-rank (Mantel-Cox) test). See FIG. 3B.

Motor circuitry studies germline Gpt2-null mice. Germline Gpt2-null mice are generated by a heterozygous breeding pair scheme that involves a male $Gpt2^{+/}$ and a female $Gpt2^{+/-}$. As described in the proposal, the procedures for motor behavior are Open Field Test, Hindlimb Clasping Reflex, Rotarod Test, Wire Hang Test, and DigiGait studies.

The average of four litters over the reproductive period of a female mouse is an average litter size of six pups, The neuropathology assays generally involve the procedure of perfusion of adult animals.

Procedures for electrophysiological studies involve EMG and muscle physiology and strength studies, as the inventors have published. See Sugita et al., Skelet. Muscle 6, 31 (2016) and Higashimori et al., Muscle Nerve, 31, 610-620 (2005).

Rescue of motor phenotype in vivo with dietary modifications. The inventors perform the procedures with and without dietary supplementation. The assay diets are standard chow; 5% alanine supplementation by weight, triheptanoin supplementation (30% caloric intake), and alanine+triheptanoin combined supplementation. In pilot assays, the inventors also test an increasing dose of alanine supplementation on a subset of outcomes (weight and survival). The amount of triheptanoin was advised by Ultragenyx, based on its experience in other preclinical studies. Depending on early results, the dosage of triheptanoin can also be varied. Diet amounts are equivalent across conditions and are given ad libitum. The genotypes tested for the diet are Gpt2-null mice vs. littermate control.

Predicted results are outlined in TABLE 1.

Regarding statistical rigor, the preliminary data are used to assess outcomes distributions. Any necessary transformations, e.g., to combat skew, are performed before the hypothesis is tested. Model-based estimates are generated using mixed-effects linear regression (animal weight, motor behavior, neuropathology, EMG studies) and time-to-event (animal survival) analysis models. Some outcomes are measured repeatedly (e.g., motor behavior outcomes) and are accommodated with random effects. To account for a multiplicity of hypothesis testing, the inventors use Benjamini and Hochberg procedure to maintain a 5% type-I error rate within a narrow domain. See Hochberg, & Benjamini, Stat. Med., 9, 811-818 (1990). The primary estimands are differences in means of outcomes measures, estimated using a mutant vs. control contrast. Missing data are accommodated by multiple imputations of missing records using algorithms that can accommodate the clustered longitudinal design. Sample size and experimental animal number vary across studies, from 6-16 biological replicates per condition, as outlined in the Vertebrate Animal Studies section, which, based on the preliminary data, provides greater than 80% power to detect standardized mean differences in the moderate to large range (0.5 to 1.1 standardized units). In studies regarding dietary supplementation, the main contrasts of interest are multicategory indicators of treatment regimen: no drug (control) vs. alanine, triheptanoin, and combination. Contrasts with control are accomplished with dummy variable coding. Contrasts across treatment regimen, e.g., dose 1 vs. dose 2, are accomplished with post hoc tests. Multiplicity controls use the method of Benjamini and Hochberg.

Sample size considerations. Sample size estimates are based on effect size and variation in the preliminary data. For some assays, exact sample size prediction is difficult. To address this, the inventors use an adaptive design technique developed by Chow & Chang, Orphanet J. Rare Dis., 3, 11 (2008). When the inventors accumulate half of the planned observations, the inventors can generate updated sample size estimates. This update does not rely on effect size but only on the estimated variance. The goal is to ensure sufficient 80% power to detect small effects, e.g., Cohen's standardized mean difference of at least 0.2.

Sex as a biological variable. Animal studies involve male and female littermates. The inventors have no prior hypotheses regarding sex differences, nor are sex-specific effects present in the data. In agreement with NIH guidance, the plan is to record results by sex, test the main hypotheses with both sexes combined, and examine the effects of sex in post hoc analyses. See NOT-OD-15-102 (Bethesda, MD: National Institutes of Health, U.S. Department of Health and Human Services).

Scientific methods that ensure robust and unbiased experimental design. Investigators are blind to genotype and manipulation. Sample exclusion/inclusion criteria are defined prospectively. Complementary methodologies and conserved across models corroborate the results.

TABLE 2

Specific Aims and Benchmarks of Success (B)

To test the efficacy of dietary high-alanine
supplementation in Gpt2-null mice.
B1a: Assessment of animal growth (weight) and survival.
B1b: Assessment of motor behavior.
B1c: Assessment of neuropathology and electrophysiology.
To test the efficacy of triheptanoin dietary
supplementation in Gpt2-null mice.
B2a: Assessment of animal growth (weight) and survival.
B2b: Assessment of motor behavior.
B2c: Assessment of neuropathology and electrophysiology.
To test the efficacy of alanine + triheptanoin
supplementations in Gpt2-null mice.
B3a: Assessment of animal growth (weight) and survival.
B3b: Assessment of motor behavior.
B3c: Assessment of neuropathology and electrophysiology.

Research limitations and contingencies. A pitfall to consider is if The inventors see no effect of supplements on outcomes. The inventors saw an impact of a high-alanine diet on animal survival. The preliminary data provide a strong premise that warrants rigorous testing of combined triheptanoin with alanine. If the inventors do not see an effect of triheptanoin alone or in combination with alanine, they would likely still go forward with alanine supplementation alone as a treatment for patients. If the inventors only see a partial response in mice, alternative strategies to pursue improved efficacy are increased dosing (greater than 5% alanine or 30% triheptanoin) or altered delivery, such as feeding by oral gavage.

Example 2

Establish a Collaborative Clinical Research Network and Develop a Protocol for Biomarker Studies and a Clinical Trial in GPT2 Disease The purpose of this EXAMPLE is to establish a collaborative clinical research network and develop a protocol for biomarker studies and a clinical trial in GPT2 disease. To prepare for a clinical trial in patients, The inventors establish a patient registry and begin a natural history investigation. The inventors are designing the protocol for a biomarker investigation and clinical trial and establish an international network of treaters. The inventors apply advanced metabolomic techniques in pilot biomarker assays. The inventors also work collaboratively with family leaders who are integrated into these research efforts. The outcomes of this EXAMPLE are the establishment of a clinical research team, patient cohort, and a clinical trial protocol designed for U.S. Food & Drug Administration benchmarks.

Enrollment of families with GPT2 disease. The inventors assessed a large group of families with GPT2 mutations to establish a core phenotype of GPT2 disease Ouyang et al., Hum. Genet., 138, 1183-1200 (2019). The core phenotype includes global developmental delay, intellectual disability (generally in the moderate range), postnatal microcephaly, epilepsy in a subset of patients (approximately 35%), small stature, and progressive spastic paraplegia.

GPT2 disease patient registry. Patients can be enrolled remotely by internet-based communication, including contacting pediatric genetic programs and genetic diagnostic laboratories nationally and internationally. Other powerful internet-based strategies involve online human genetic databases such as ClinVar. The identified patient guardian provides written informed consent. The goal for this stage of research is establishing a registry of approximately twenty-thirty patients with GPT2 disease.

Natural history of GPT2 disease and identification of target symptoms. The inventors are establishing the data collection required for the first steps in a natural history investigation in GPT2 disease. This data collection assists in identifying the ideal target symptoms to be followed during a clinical trial and in understanding age ranges at which target symptoms can be observed. The inventors collect data remotely through online assessments. Data collected include demographic information; a standardized Medical and Family History Questionnaire; a standardized Epilepsy Questionnaire; an assessment of adaptive function (Vineland Adaptive Behavioral Scales-II); and the Aberrant Behavior Checklist. The inventors also collect medical records from specialists and review these data as a multidisciplinary team using a standardized data extraction protocol.

Development of an international network of treaters and planning of the clinical trial protocol and biomarker investigation: Based on tertiary centers wherein current GPT2 patients are receiving treatment, the inventors are assembling a network of clinicians who will follow patients with GPT2 disease in future clinical studies. The inventors are designing select sites that are regional to patients, determine site doctors, and develop a clinical research protocol. The inventors are also consulting with NIH Intramural Program to explore the possibility of conducting the core assessments and trials in person at the NIH Clinical Research Center. The inventors can move instead to work with Clinical Research Organizations (CROs).

During the development of clinical investigation protocols, the inventors conduct a pilot biomarker investigation using advanced metabolomics methods in the University of Texas Southwestern Metabolomics Core, which has conducted metabolomics studies on plasma collected at the University of Texas Southwestern from approximately 800 children, generally newborns to age five years. The Metabolomics Core also has patient samples from national and international locations. The inventors can identify GPT2 disease patients from the registry. Plasma can be collected and analyzed. Human patients with GPT2 disease have low alanine in their plasma. See Celis et al., J. Inherit. Metab. Dis., 38, 941-948 (2015).

Predicted results and statistical analysis plan. Based on the clinical data collection, the inventors are identifying the target symptoms and age ranges to follow treatment responses in a clinical trial. The predictions are that target symptoms include quantitative measures of adaptive function, focusing on motor function and cognitive tasks and behavior.

The metabolome of the patients with GPT2 disease is compared to the large UT Southwestern dataset. In addition to metabolome-wide exploratory analyses, the inventors are testing specifically targeted hypotheses such as low alanine or low tricarboxylic acid cycle intermediates. With the natural history investigation, the inventors generate sufficient natural history data to compare the treatment to patient baseline without necessitating an investigation design requiring a control arm to meet U.S. Food & Drug Administration benchmarks.

TABLE 3

Specific Aims and Benchmarks of Success (B)

To establish a GPT2 disease family registry
B1a: Re-contact with families from the
inventors' prior studies.
B1b: Recruitment nationwide and
internationally in a systematic fashion.
To establish the clinical research network.
B2a: Engagement with clinical treaters of
patients with GPT2 disease nationally.
B2b: Development of family association for
GPT2 disease with families as collaborators.
B2c: Sharing of data and consultation
with the NIH Intramural Program.
B2d: Sharing of data and consultation with Ultragenyx.
To establish the natural history
investigation for GPT2 disease
B3a: Collection of baseline clinical
data on GPT2 disease patients.
B3b: Establishment of natural history investigation
protocol and measures of target symptoms.
To establish the protocol for clinical
biomarker investigation and clinical trial.
B4a: Determination of the location of the
clinical sites and clinical site PIs and teams.
B4b: Pilot studies of metabolomics on
plasma in GPT2 disease at UT Southwestern.
B4c: Development of the biomarker
investigation and clinical trial protocol.

LIST OF ADDITIONAL EMBODIMENTS

Specific compositions and methods of treating metabolic dysfunction and neurological disease with developmental and progressive features have been described. The detailed description in this specification is illustrative and not restrictive or exhaustive. The detailed description is not intended to limit the disclosure to the precise form disclosed. Other equivalents and modifications besides those already described are possible without departing from the inventive concepts described in this specification, as those skilled in the medical art recognize. When the specification or claims recite method steps or functions in an order, alternative embodiments may perform the functions in a different order or substantially concurrently. Therefore, the inventive subject matter is not to be restricted except in the spirit of the disclosure.

When interpreting the disclosure, all terms should be interpreted in the broadest possible manner consistent with the context. Unless otherwise defined, all technical and scientific terms used in this specification have the same meaning as commonly understood by a person having ordinary skill in the medical art. This invention is not limited to the particular methodology, protocols, reagents, and the like described in this specification and, as such, can vary in practice. The terminology used in this specification is not intended to limit the scope of the invention, which is defined solely by the claims.

When a range of values is provided, each intervening value, to the tenth of the unit of the lower limit, unless the context dictates otherwise, between the upper and lower limit of that range and any other stated or intervening value in that range of values.

Some embodiments of the technology described can be defined according to the following numbered paragraphs:

1. A method of screening for a therapeutic compound for use in treating metabolic dysfunction or neurological disease with developmental and progressive features, using a Gpt2-null mouse model.

2. Alanine, for use in treating metabolic dysfunction or neurological disease with developmental and progressive features.

3. An anaplerotic supplement (such as triheptanoin) for use in treating metabolic dysfunction or neurological disease with developmental and progressive features.

4. A method of treating metabolic dysfunction or neurological disease with developmental and progressive features, comprising the step of administering a compound selected from the group consisting of alanine and an anaplerotic supplement (such as triheptanoin).

5. A method of screening newborn humans for metabolic dysfunction or neurological disease with developmental and progressive features, comprising the step of screening the newborns for a Gpt2 mutation or a deficiency in the glutamate pyruvate transaminase 2 (GPT2) enzyme.

CITATION LIST

A person having ordinary skill in the medical art can use these patents, patent applications, and scientific references as guidance to predictable results when making and using the invention.

Patent Literature

U.S. Pat. Publ. 2016/0265057 A1 (Smith), Markers for amyotrophic lateral sclerosis (ALS) and presymptomatic Alzheimer's disease (PSAD), discloses useful drug screening methods.

Non-Patent Literature

Aman et al., (The Aberrant Behavior Checklist: a behavior rating scale for the assessment of treatment effects. Am. J. Ment. Defic., 89, 485-491 1985).

Arlotta et al., Neuronal subtype-specific genes that control corticospinal motor neuron development in vivo. Neuron, 45, 207-221 (2005).

Battaglia & Regnault, Placental transport and metabolism of amino acids. Placenta, 22, 145-161 (2001).

Blackstone, Cellular pathways of hereditary spastic paraplegia. Annu. Rev. Neurosci., 35, 25-47 (2012).

Boyko et al., Brain to blood glutamate scavenging as a novel therapeutic modality: A review. J. Neural Transm. (Vienna) 121 (8), 971-979 (2014). This review publication shows that the level of blood glutamate is a neurological therapeutic target.

Camp et al., Phenylketonuria scientific review conference: State of the science and future research needs. Mol. Genet. Metab., 112, 87-122 (2014).

Celis et al., Loss of function mutation in glutamic pyruvate transaminase 2 (GPT2) causes developmental encephalopathy. J. Inherit. Metab. Dis., 38, 941-948 (2015).

Centers for Disease Control and Prevention, Economic costs associated with mental retardation, cerebral palsy, hearing loss, and vision impairment--United States, 2003. MMWR Morbidity & Mortality Weekly Report, 53, 57-59 (2004).

Chow & Chang, Adaptive design methods in clinical trials-a review. Orphanet J. Rare Dis., 3, 11 (2008).

Connell & Reid, Quantitative gait analysis using a motorized treadmill system sensitively detects motor abnormalities in mice expressing ATPase defective spastin. PLOS One, 11, e0152413 (2016).

Consideration of sex as a biological variable in NIH-funded research. In NOT-OD-15-102 (Bethesda, MD: National Institutes of Health, U.S. Department of Health and Human Services).

Fink & Cafferty, Reorganization of intact descending motor circuits to replace lost connections after injury. Neurotherapeutics 13, 370-381 (2016).

Fink, Hereditary spastic paraplegia: clinical principles and genetic advances. Semin. Neurol., 34, 293-305 (2014).

Fink, Strittmatter, & Cafferty, Comprehensive corticospinal labeling with mu-crystallin transgene reveals axon regeneration after spinal cord trauma in ngr1-/- mice. J. Neurosci., 35, 15403-15418 (2015).

Francis, Markov, & Leone, Dietary triheptanoin rescues oligodendrocyte loss, dysmyelination and motor function in the nur7 mouse model of Canavan disease. J. Inherit. Metab. Dis., 37, 369-381 (2014).

Genc, Gozutok, & Ozdinler, Complexity of generating mouse models to study the upper motor neurons: Let us shift focus from mice to neurons. Int. J. Mol. Sci. 20 (2019).

Guide for the Care and Use of Laboratory Animals, 8th edition (Washington, DC: The National Academies Press).

Hadera et al., Triheptanoin partially restores levels of tricarboxylic acid cycle intermediates in the mouse pilocarpine model of epilepsy. J. Neurochem., 129, 107-119 (2014).

Hao et al., Oncogenic PIK3CA mutations reprogram glutamine metabolism in colorectal cancer. Nature Commun., 7, 11971 (2016).

Hengel et al., GPT2 mutations cause developmental encephalopathy with microcephaly and features of complicated hereditary spastic paraplegia. Clin. Genet., 94, 356-361 (2018).

Higashimori et al., Peripheral axon caliber and conduction velocity are decreased after burn injury in mice. Muscle Nerve, 31, 610-620 (2005).

Hochberg & Benjamini, More powerful procedures for multiple significance testing. Stat. Med., 9, 811-818 (1990).

Kaymakcalan et al., Novel compound heterozygous mutations in GPT2 linked to microcephaly, and intellectual developmental disability with or without spastic paraplegia. Am. J. Med. Genet. A, 176, 421-425 (2018).

Kim et al. Mitochondrial GPT2 plays a pivotal role in metabolic adaptation to the perturbation of mitochondrial glutamine metabolism. Oncogene, 38, 4729-4738 (2019).

Landrum et al., ClinVar: public archive of interpretations of clinically relevant variants. Nucleic Acids Res., 44, D862-868 (2016).

Landrum et al., ClinVar: public archive of relationships among sequence variation and human phenotype. Nucleic Acids Res., 42, D980-985 (2014).

Liang, Paxinos, & Watson, The red nucleus and the rubrospinal projection in the mouse. Brain Struct. Funct., 217, 221-232 (2012).

Lobo-Prada et al., A homozygous mutation in GPT2 associated with nonsyndromic intellectual disability in a consanguineous family from Costa Rica. JIMD Rep., 36, 59-66 (2017).

Maxwell et al., alpha-Motor neurons are spared from aging while their synaptic inputs degenerate in monkeys and mice. Aging Cell, 17 (2018).

National Research Council of the National Academies (2011).

O'Kane et al., Na+-dependent neutral amino acid transporters A, ASC, and N of the blood-brain barrier: mechanisms for neutral amino acid removal. Am. J. Physiol. Endocrinol. Metab., 287, E622-629 (2004).

Oldendorf, Brain uptake of radiolabeled amino acids, amines, and hexoses after arterial injection. Am. J. Physiol., 221, 1629-1639 (1971).

Ouyang et al., GPT2 mutations in autosomal recessive developmental disability: extending the clinical phenotype and population prevalence estimates. Hum. Genet., 138, 1183-1200 (2019).

Ouyang et al., Mutations in mitochondrial enzyme GPT2 cause metabolic dysfunction and neurological disease with developmental and progressive features. Proc. Natl. Acad. Sci. U.S.A., 113 (38), E5598-E5607 (Sep. 20, 2016). Autosomal recessive mutations in the enzyme glutamate pyruvate transaminase 2 (GPT2) in a neurological syndrome involving intellectual disability, reduced brain growth, and progressive motor symptoms inactivate the enzyme. GPT2 catalyzes the reversible addition of an amino group from glutamate to pyruvate, yielding alanine and a-ketoglutarate. The GPT2 gene demonstrates expression in the brain postnatally, and the protein localizes to mitochondria. As in humans, Gpt2-null mice exhibit reduced brain growth. Mutant mouse brains show abnormal metabolite levels, including amino acid metabolism pathways, the tricarboxylic acid cycle, and neuroprotective mechanisms. This investigation identifies GPT2 as an important mitochondrial enzyme in disease with general relevance to developmental and potentially to neurodegenerative mechanisms.

Owen, Kalhan, & Hanson, The key role of anaplerosis and cataplerosis for citric acid cycle function. J. Biol. Chem., 277, 30409-30412 (2002).

Ozdinler et al., Corticospinal motor neurons and related subcerebral projection neurons undergo early and specific neurodegeneration in hSOD1G (9) (3) A transgenic ALS mice. J. Neurosci., 31, 4166-4177 (2011).

Park et al., Anaplerotic triheptanoin diet enhances mitochondrial substrate use to remodel the metabolome and improve lifespan, motor function, and sociability in MeCP2-null mice. PLOS One, 9, e109527 (2014).

Schmued & Hopkins, Fluoro-Jade B: A high affinity fluorescent marker for the localization of neuronal degeneration. Brain Res., 874, 123-130 (2000).

Smith et al., Addiction to coupling of the Warburg effect with glutamine catabolismin cancer cells. Cell. Rep., 17, 821-836 (2016).

Sparrow, Balla, & Cicchetti, Vineland Adaptive Behavior Scales, Second Edition (Shoreview, MN: American Guidance Service) (2005).

Sugita et al. VAChT overexpression increases acetylcholine at the synaptic cleft and accelerates aging of neuromuscular junctions. Skelet. Muscle 6, 31 (2016).

Valdez et al., Attenuation of age-related changes in mouse neuromuscular synapses by caloric restriction and exercise. Proc. Natl. Acad. Sci. U.S.A., 107, 14863-14868 (2010).

Vockley et al., UX007 for the treatment of long chain-fatty acid oxidation disorders: Safety and efficacy in children and adults following 24 weeks of treatment. Mol. Genet. Metab., 120, 370-377 (2017).

Willis et al., Anticonvulsant effects of a triheptanoin diet in two mouse chronic seizure models. Neurobiol. Dis., 40, 565-572 (2010).

Yamaguchi & Shen, Histological analysis of neurodegeneration in the mouse brain. Methods Mol. Biol., 1004, 91-113 (2013).

Zhu et al., Ablation of NF1 function in neurons induces abnormal development of cerebral cortex and reactive gliosis in the brain. Genes Dev 15, 859-876 (2001).

TEXTBOOKS AND TECHNICAL REFERENCES

Current Protocols in Immunology (CPI) (2003). John E. Coligan, ADA M Kruisbeek, David H Margulies, Ethan M Shevach, Warren Strobe, (eds.) John Wiley and Sons, Inc. (ISBN 0471142735, 9780471142737).

Current Protocols in Molecular Biology (CPMB), (2014). Frederick M. Ausubel (ed.), John Wiley and Sons (ISBN 047150338X, 9780471503385).

Current Protocols in Protein Science (CPPS), (2005). John E. Coligan (ed.), John Wiley and Sons, Inc.

Immunology (2006). Werner Luttmann, published by Elsevier.

Janeway's Immunobiology, (2014). Kenneth Murphy, Allan Mowat, Casey Weaver (eds.), Taylor & Francis Limited, (ISBN 0815345305, 9780815345305).

Laboratory Methods in Enzymology: DNA, (2013). Jon Lorsch (ed.) Elsevier (ISBN 0124199542).

Lewin's Genes XI, (2014). published by Jones & Bartlett Publishers (ISBN-1449659055).

Molecular Biology and Biotechnology: a Comprehensive Desk Reference, (1995). Robert A. Meyers (ed.), published by VCH Publishers, Inc. (ISBN 1-56081-569-8).

Molecular Cloning: A Laboratory Manual, 4th ed., Michael Richard Green and Joseph Sambrook, (2012). Cold Spring Harbor Laboratory Press, Cold Spring Harbor, N.Y., USA (ISBN 1936113414).

The Encyclopedia of Molecular Cell Biology and Molecular Medicine, Robert S. Porter et al. (eds.), published by Blackwell Science Ltd., 1999-2012 (ISBN 9783527600908).

The Merck Manual of Diagnosis and Therapy, 19th edition (Merck Sharp & Dohme Corp., 2018).

Pharmaceutical Sciences $23^{rd}$ edition (Elsevier, 2020).

All patents and publications cited throughout this specification are expressly incorporated by reference to disclose and describe the materials and methods that might be used with the technologies described in this specification. The publications discussed are provided solely for their disclosure before the filing date. They should not be construed as an admission that the inventors may not antedate such disclosure under prior invention or for any other reason. If there is an apparent discrepancy between a previous patent or publication and the description provided in this specification, the present specification (including any definitions) and claims shall control. All statements as to the date or representation as to the contents of these documents are based on the information available to the applicants and constitute no admission as to the correctness of the dates or contents of these documents. The dates of publication provided in this specification may differ from the actual publication dates. If there is an apparent discrepancy between a publication date provided in this specification and the actual publication date supplied by the publisher, the actual publication date shall control.

I claim:

1. A method of treating a GPT2 deficiency in a subject in need thereof, the method comprising the step of:
   (1) administering a therapeutically effective amount of alanine and an anaplerotic supplement comprising triheptanoin to the subject;
       whereby the administration of the therapeutically effective amount in step (1) results in an improvement in the subject's GPT2 deficiency; wherein the improvement can be measured by an assay for motor circuitry development and function comprising an assay for motor behavior.

2. The method of claim 1, wherein the therapeutically effective amount of alanine and the anaplerotic supplement consists of alanine and triheptanoin.

3. The method of claim 1, wherein the GPT2 deficiency is selected from a GPT2 mutation from a large group of families with GPT2 mutations.

4. The method of claim 1, wherein the GPT2 deficiency is selected from a GPT2 mutation in a GPT2 disease patient database.

* * * * *